United States Patent [19]

Kyo et al.

[11] 3,947,504

[45] Mar. 30, 1976

[54] SEPARATION AND RECOVERY OF 3-METHYL-3-BUTENE-1-OL

[75] Inventors: Sunao Kyo; Hideaki Oka; Katsuhiko Hayashi; Hidetsugu Tanaka, all of Ibaragi, Japan

[73] Assignee: Kuraray Co., Ltd., Kurashiki, Japan

[22] Filed: Feb. 27, 1974

[21] Appl. No.: 446,421

[30] Foreign Application Priority Data

Mar. 8, 1973 Japan.............................. 48-27791

[52] U.S. Cl....... 260/643 A; 260/340.7; 260/462 R; 260/639 B
[51] Int. Cl.²........................................ C07C 29/24
[58] Field of Search................................ 260/643 A

[56] References Cited
UNITED STATES PATENTS

| | | | |
|---|---|---|---|
| 2,068,415 | 1/1937 | Klipstein........................ | 260/643 A |
| 2,305,236 | 12/1942 | Bruson........................... | 260/643 A |
| 2,885,446 | 5/1959 | Sharp et al...................... | 260/643 A |
| 2,997,480 | 8/1961 | Hellin et al..................... | 260/340.7 |
| 3,060,239 | 10/1962 | Hellin et al..................... | 260/606 |
| 3,221,075 | 11/1965 | Hamamoto et al................ | 260/601 |

FOREIGN PATENTS OR APPLICATIONS 1,376,474   9/1964   France

OTHER PUBLICATIONS

Bulletin de la Societe Chinique de France, 1963 (12) pp. 2722–2725.
Hellin et al., "Bulletin de la Societe Chimique de France," 1963 (12), pp. 2725–2734.
Hellin et al., "Bulletin de la Societe Chimique de France," 1964 (4) pp. 800–804.

*Primary Examiner*—Joseph E. Evans
*Attorney, Agent, or Firm*—Bacon & Thomas

[57]   ABSTRACT

The 3-methyl-3-butene-1-ol contained in the oily mixture obtained in the production of isoprene by the reaction of isobutene and formaldehyde through the intermediate 4,4-dimethyl-1,3-dioxane can be isolated by adding boric acid to said mixture to form the boric acid ester of 3-methyl-3-butene-1-ol and recovering the higher boiling fraction having a boiling point of above 160°C.

6 Claims, No Drawings

SEPARATION AND RECOVERY OF 3-METHYL-3-BUTENE-1-OL

BACKGROUND OF THE INVENTION

1. Field of the Invention

This invention relates to a process for the separation and the recovery of 3-methyl-3-butene-1-ol which is formed, as a by-product, during the production of isoprene by the reaction of isobutene and formaldehyde.

2. Description of the Prior Art

It is well known that 4,4-dimethyl-1,3-dioxane (useful as an intermediate for the production of isoprene) may be synthesized by the Prins reaction wherein isobutene is condensed with formaldehyde in an aqueous medium in the presence of an acid catalyst such as sulfuric acid, phosphoric acid or sulfonic acid at a temperature of 20° to 100°C. Such a method is described in, for example, U.S. Pat. No. 2,997,480. It is also well known that the above dioxane decomposes in the presence of acidic catalysts to give isoprene as described in, for example, U.S. Pat. Nos. 3,060,239 and 3,221,075 and British Pat. No. 884,809. In the production of isoprene by the reaction of isobutene and formaldehyde through the intermediate 4,4-dimethyl-1,3-dioxane as mentioned above, 3-methyl-3-butene-1-ol is formed as a by-product.

Since the boiling point of 3-methyl-3-butene-1-ol (boiling point: 130°–131°C.) is very close to that of 4,4-dimethyl-1,3-dioxane (boiling point: 133°C.), it is difficult to separate them and recover said alcohol from said dioxane by a conventional distillation operation. Therefore, in the production of isoprene by the above method, the by-product 3-methyl-3-butene-1-ol inevitably accompanies the 4,4-dimethyl-1,3-dioxane cycled in the reaction system and both are converted to isoprene according to the following equations:

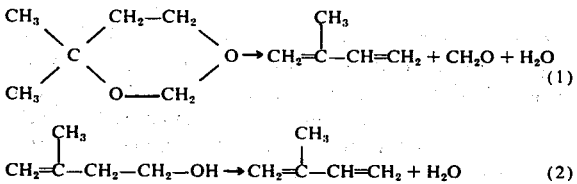

SUMMARY OF THE INVENTION

The primary object of the present invention is to provide a process for separating and recovering 3-methyl-3-butene-1-ol from the reaction mixture obtained in a process of isoprene production by the reaction of isobutene and formaldehyde.

Another object of the present invention is to isolate 3-methyl-3-butene-1-ol from said mixture for the utilization of the same in applications other than the preparation of isoprene.

Other objects and advantages will become apparent from the ensuing description.

According to the present invention, a process is provided for the separation and recovery of 3-methyl-3-butene-1-ol from an oily mixture having a boiling point not lower than 85°C. at atmospheric pressure which is obtained in the production of isoprene by the reaction of isobutene and formaldehyde through the intermediate 4,4-dimethyl-1,3-dioxane, which comprises the steps of (1) heating said mixture in the presence of boric acid or boric acid anhydride, (2) removing the fraction boiling at a temperature not higher than 160°C. under atmospheric pressure from the so-treated mixture and (3) recovering 3-methyl-3-butene-1-ol from the residue.

DESCRIPTION OF THE PREFERRED EMBODIMENTS

The term "oily mixture having a boiling point not lower than 85°C. at atmospheric pressure" as used herein is intended to mean the organic mixture boiling at 85°C. or higher which is obtained (by a conventional separating method such as distillation) from the organic layer contained in the reaction mixture originating from (i) the reaction of isobutene and formaldehyde (in a molar ratio of 10 to 0.2 moles of isobutene per mole of formaldehyde) to produce 4,4-dimethyl-1,3-dioxane in an aqueous medium in the presence of an acid catalyst such as sulfuric acid, phosphoric acid or sulfonic acid at a temperature of 20° to 100°C. and/or (ii) the decomposition reaction of 4,4-dimethyl-1,3-dioxane into isoprene at a temperature of 150° to 400°C. in the presence of an acidic catalyst.

Since both of these procedures (i) and (ii) are known per se, no detailed description of the same will be given herein. The disclosure of U.S. Pat. No. 2,997,480 (which describes the first procedure) is expressly incorporated herein by reference. It is the intention to cover all "acid" catalysts useful in such a process, the specific ones disclosed above merely being exemplary.

The acidic catalyst suitable for the decomposition of 4,4-dimethyl-1,3-dioxane is, for example, phosphoric acid, phosphates, metal oxides, metal sulfates, etc., if desired deposited on (or incorporated in) a carrier substance such as crystallized silica, silicon carbide or a clay. The most preferred acidic catalyst is phosphoric acid deposited on silica gel, quartz, kaolin or diatomaceous earth as a carrier; i.e., the so-called solid phosphoric acid catalyst which has been calcined at a temperature of from 700° to 1100°C. However, any "acidic catalyst" known to be useful in such a process can be used, it being the intention not to limit the catalyst to those exemplified above. Reference is made to U.S. Pat. Nos. 3,060,239 and 3,331,075 and to British Pat. No. 884,809 for a fuller description of this process and more catalysts.

Generally stated, the process of the present invention may employ as a starting material any reaction mixture obtained by the above known processes (i) and (ii). It is the intention not to limit the starting material of the invention to only specific reaction mixtures produced by these processes, but rather to include all such reaction mixtures produced by the above processes (i) and (ii) as broadly described above.

The oily mixture having a boiling point not lower than 85°C. contains 4,4-dimethyl-1,3-dioxane as the predominant component and also, higher boiling products, for example, methyl isopropyl ketone (boiling point: 94°C.), 4-methylene tetrahydropyran (boiling point: 109°C.), 4-methyl-5,6-dihydro-α-pyran (boiling point: 119°C.), 3-methyl-3-butene-1-ol and isoprene oligomer, etc., in variable relative proportions according to the conditions employed in the isoprene production process. Generally speaking, the amounts of the components in the oily mixture may fall within the following range; 4,4-dimethyl-1,3-dioxane: 30–80 wt. %, methyl isopropyl ketone: 1–6 wt. %, 4-methylene tetrahydropyran: 2–7 wt. %, 4-methyl-5,6-dihydro-α- pyran: 4–10 wt. %, 3-methyl-3-butene-1-ol: 0.3–40 wt. %, trioxane: 1–1.5 wt. %, 2-methyl butanal: 2–3 wt. %, 4-ethyl-1,3-dioxane: 0.1–1.5 wt. % and the other components: 3–10 wt. %, wherein weight percent is based on the weight of the oily mixture. Said mixture may further contain a number of components having wide ranges of boiling points extending even to resinous materials.

The content of 3-methyl-3-butene-1-ol in the above mixture is generally within the range of from 0.5 to 25% by weight, based on the weight of the mixture. The process of the present invention can be applied not only to said oily mixture directly but also to the mixture obtained by the conventional distillation of the oily mixture which essentially consists of 4,4-dimethyl-1,3-dioxane and 3-methyl-3-butene-1-ol in respective amounts of 99 to 10 wt. % and 1 to 90 wt. % (boiling point of this distillate: 129°–133°C.).

As is known, 1,3-dioxane compounds are unstable under acidic conditions and dioxane ring cleavage reactions easily occur induced by, for example, hydrolysis. Copending U.S. application Ser. No. 420,849 filed Dec. 3, 1973, by the same inventors discloses that the ring of 1,3-dioxane compounds having at least one hydroxyl group is easily subjected to cleavage by the action of a weak acid such as boric acid. The disclosure of said copending application is hereby expressly incorporated herein by reference.

According to the present invention, however, when the mixture comprising 4,4-dimethyl-1,3-dioxane as the main component and a hydroxyl-containing compound such as 3-methyl-3-butene-1-ol is heated in the presence of added boric acid, said 1,3-dioxane does not undergo any change. This fact is quite surprising considering the above prior teachings. The reason for it is not presently clear, but it may be considered that the hydroxyl-containing compound in the mixture used in the invention forms high boiling boric acid esters and water by the reaction with boric acid or boric acid anhydride, and hence 4,4-dimethyl-1,3-dioxane, the main component, does not undergo the above change at all despite the presence of water in the reaction mixture.

In consequence, according to the present invention, when boric acid or boric acid anhydride is added to the oily mixture boiling at and above 85°C. comprising 4,4-dimethyl-1,3-dioxane as a major component and 3-methyl-3-butene-1-ol, and then the fraction boiling at not higher than 160°C. is distilled off after heating, 4,4-dimethyl-1,3-dioxane and other materials having a boiling point close to that of 3-methyl-3-butene-1-ol are removed as the distillates from said mixture to leave the boric acid ester of 3-methyl-3-butene-1-ol and other higher boiling materials of boiling points above 160°C. as the residue. The full recovery of 3-methyl-3-butene-1-ol can be accomplished from said residue. Thus, according to the present invention, 3-methyl-3-butene-1-ol can be easily separated and recovered from the oily mixture which has been obtained in the production of isoprene by the reaction of isobutene and formaldehyde, without bringing about substantial changes in each component.

The amount of boric acid added to the oily mixture (and correspondingly, the amount of boric acid anhydride which is converted into boric acid) is preferably not more than 2 mole, more preferably one-third to one-half mole, per mole of 3-methyl-3-butene-1-ol contained in the oily mixture. If said molar ratio is below one-third, the full recovery of 3-methyl-3-butene-1-ol cannot be expected and if said molar ratio exceeds 1, the process tends toward economic disadvantages due to the increase in the amount of boric acid to be cycled in the process of the invention. However, the process is operable with amounts of boric acid and boric acid anhydride outside of the above limits, and it is not the intention to limit the broad invention to the preferred limits.

The heating of the oily mixture after the addition of the boric acid or boric acid anhydride is preferably carried out at the boiling temperature of said mixture, namely its reflux temperature, which varies in general from 92° to 160°C. under atmospheric pressure. The heating may also be effected under elevated or reduced pressure. Generally, however, this heating step is performed at a temperature and for a period of time necessary to complete the reaction of the boric acid or boric acid anhydride with the alcohol to form the boric acid ester thereof. Upon heating, boric acid is reacted with 3-methyl-3-butene-1-ol to generate water which forms an azeotropic mixture with 4,4-dimethyl-1,3-dioxane. Therefore, the heating can be carried out in a manner such that said azeotropic mixture is distilled off during the heating, or the aqueous phase may be removed from the thus-separated and subsequently condensed azeotropic mixture and the remaining organic phase may be returned to the reaction system during the heating. As a result, the temperature of the reaction liquid is increased. Boric acid anhydride may be converted into boric acid under the reaction conditions. The completion of the reaction may be recognized as that point where the formation of the azeotropic mixture substantially ceases. It takes about 1 to 2 hours to complete the reaction generally.

After the above reaction with heating, the reaction mixture is distilled under normal or reduced pressure to remove those components which boil at 160°C. or lower at atmospheric pressure while leaving as a residue those components which boil above 160°C., the residue predominantly comprising the boric acid ester of 3-methyl-3-butene-1-ol. The boric acid ester of 3-methyl-3-butene-1-ol, which can be isolated from said residue by further distillation, is a novel, unknown substance in the literature, and it is a colorless, transparent liquid having a boiling point of 74° to 76°C. at a reduced pressure of 0.07 mmHg, which can easily be subjected to hydrolysis under the influence of the humidity in the air.

The separation and recovery of 3-methyl-3-butene-1-ol may be conducted in a manner as above mentioned, but the recovery of the same can be facilitated by contacting the residue (which boils above 160°C.) with water in the form of liquid water or steam to effect hydrolysis. Especial operational advantages can be obtained by blowing steam into the residue whereby the 3-methyl-3-butene-1-ol is steam distilled (boiling point of the azeotropic mixture: 95°C.). After hydrolysis, boric acid can be recovered by concentration from the aqueous layer in a form suitable for reuse, and the concentrated water also can be reused for the hydrolysis step resulting in the prevention of loss of 3-methyl-3-butene-1-ol from the residue.

3-methyl-3-butene-1-ol separated according to the present invention is the simplest isoprenoid alcohol and is a useful industrial material. For example, it can be employed as a starting or intermediate material in the production of perfumes, medicines and synthetic polymers.

The presently preferred and practical embodiments of the present invention are illustratively shown in the following examples. All parts and percentages (%) are "by weight" except as otherwise indicated.

EXAMPLE 1

16.2G of boric acid was added to 90g of a mixture consisting of 38% of 3-methyl-3-butene-1-ol and 62% of 4,4-dimethyl-1,3-dioxane. After the mixture was heated to reflux for 3 hours, the mixture was subjected to distillation under a reduced pressure of 64 mm Hg until the temperature of the liquid rose to 145°C. 67.1G of the distillate was obtained. By a gas-liquid chromatographic analysis, the distillate was found to comprise a mixture of 4.37g of 3-methyl-3-butene-1-ol, 53.3g of 4,4-dimethyl-1,3-dioxane (recovery: 95.6%) and water.

The residue produced by the distillation, that is 31g of a yellow transparent liquid, was mixed with 30ml of water, and the mixture was then heated to reflux for 1 hour. The resulting organic layer and aqueous layer were respectively subjected to gas-liquid chromatographic analyses. The organic layer, in which 4,4-dimethyl-1,3-dioxane could not be detected, consisted of 24.7g of 3-methyl-3-butene-1-ol and water. The aqueous layer was found to contain 3.6g of 3-methyl-3-butene-1-ol. Upon concentration of said aqueous layer under reduced pressure, 16g of boric acid in the form of crystals were recovered.

EXAMPLE 2

The starting material used in this example comprised a mixture having the composition shown in the following Table 1, which was obtained in the production of isoprene, through the intermediary of 4,4-dimethyl-1,3-dioxane, by the reaction of isobutene and formaldehyde.

1900 Parts of the above mixture and 26.9 parts of boric acid were charged to a reactor equipped with a thermometer, a stirrer and a decanter, and heated to reflux. The formed water was taken out of the decanter and the organic layer was recycled to the reactor. The distillation of the formed water terminated in about one hour. The amount of the distilled water was 29.7 parts and it contained 0.38% of 3-methyl-3-butene-1-ol and 15.1% of 4,4-dimethyl-1,3-dioxane according to a gas-liquid chromatographic analysis.

Next, the fraction boiling up to 63°C. at a pressure of 52mm Hg was distilled off from the reaction liquid under moisture-free conditions. In this case, the final temperature of the liquid reached 139°C.; the amount of the distillate was 1778 parts; and the amount of residue on distillation was 139 parts. The composition of the distillate according to a determination of gas-liquid chromatography is also shown in Table 1 from which it will be understood that substantially the entire amount of each component in the charge stock was recovered.

Table 1

| Component | Composition (parts) | |
|---|---|---|
| | Charge stock | Distillate |
| 4,4-dimethyl-1,3-dioxane | 1716 | 1704 |
| methyl isopropyl ketone | 2.1 | 1.3 |
| 4-methyl-5,6-dihydro-α-pyran | 41.5 | 40.8 |
| 4-methylene tetrahydropyran | 2.3 | 2.2 |
| trioxane | 12.7 | 12.3 |
| 3-methyl-3-butene-1-ol | 85.1 | 4.6 |

Table 1-continued

| Component | Composition (parts) | |
|---|---|---|
| | Charge stock | Distillate |
| higher boiling materials | 41.3 | 2.3 |

Then, 79 parts of the above residue was subjected to steam distillation at 95° to 100°C. using conventional apparatus. In the distilled liquid (i.e., both of the organic layer and the aqueous layer), there was formed 43.7 parts of 3-methyl-3-butene-1-ol but the other components were present only in minute quantities according to gas-liquid chromatographic analysis. On the other hand, 60 parts of the same residue was distilled under a reduced pressure of 0.07 mm Hg using conventional distillation apparatus to give 43.6 parts of the boric acid ester of 3-methyl-3-butene-1-ol (boiling point: 71°–76°C/0.07 mm Hg) and a small amount of low boiling material. 14.1 Parts of a tar-like material was produced as a bottoms product.

While the invention has been described by reference to preferred embodiments thereof, it is to be understood that various changes, modifications and/or substitutions may be made therein without departing from the spirit and scope thereof, it being the intention that the invention be limited only by the scope of the appended claims.

What is claimed is:

1. A process for the separation and the recovery of 3-methyl-3-butene-1-ol from an oily mixture containing the same and 4,4-dimethyl-1,3-dioxane, which mixture is obtained during the production of isoprene by the reaction of isobutene and formaldehyde through the intermediate 4,4-dimethyl-1,3-dioxane, said oily mixture having a boiling point not lower than 85°C at atmospheric pressure, which process comprises the steps of (1) heating at a temperature ranging between about 92° to 160°C said oily mixture in the presence of one-third to one-half mole of boric acid or boric acid anhydride per mole of 3-methyl-3-butene-1-ol contained in said oily mixture while eliminating the generated water azeotropically with 4,4-dimethyl-1,3-dioxane, (2) removing therefrom a first fraction by distillation which boils at a temperature not higher than 160°C at atmospheric pressure to separate the fraction containing 4,4-dimethyl-1,3-dioxane from a second fraction containing boric acid ester of 3-methyl-3-butene-1-ol, (3) recovering the second fraction remaining and (4) isolating 3-methyl-3-butene-1-ol therefrom.

2. The process of claim 1, wherein said oily mixture is obtained by the decomposition reaction of 4,4-dimethyl-1,3-dioxane into isoprene at a temperature of 150° to 400°C. in the presence of an acidic catalyst.

3. The process of claim 1, wherein said oily mixture is obtained by the reaction of isobutene and formaldehyde in the preparation of 4,4-dimethyl-1,3-dioxane in an aqueous medium in the presence of an acid catalyst at a temperature of 20° to 100°C.

4. The process of claim 1, wherein said oily mixture contains 4,4-dimethyl-1,3-dioxane as a major component, and methyl isopropylketone, 3-methyl butanol, 4-methylene tetrahydropyran, 4-methyl-5,6-dihydro-α-pyran, 3-methyl-3-butene-1-ol and tar-like materials.

5. The process of claim 1, wherein said oily mixture consists essentially of 4,4-dimethyl-1,3-dioxane and 3-methyl-3-butene-1-ol.

6. The process of claim 4, wherein said 3-methyl-3-butene-1-ol is present in said oily mixture in an amount of 0.5 to 25% by weight, based on the weight of said oily mixture.

* * * * *